(12) United States Patent
Koo et al.

(10) Patent No.: US 11,592,721 B2
(45) Date of Patent: Feb. 28, 2023

(54) BLACK ELECTROCHROMIC COMPOUND, AND ELECTROLYTE-INTEGRATED RADIATION CURABLE ELECTROCHROMIC COMPOSITION AND ELECTROCHROMIC DEVICE WHICH CONTAIN SAME

(71) Applicant: LG ELECTRONICS INC., Seoul (KR)

(72) Inventors: Sangmo Koo, Seoul (KR); Sooyeun Kim, Seoul (KR); Koun Park, Seoul (KR); Gukhwan An, Seoul (KR); Sanggeun Cho, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 678 days.

(21) Appl. No.: 16/481,026

(22) PCT Filed: May 15, 2017

(86) PCT No.: PCT/KR2017/005011
§ 371 (c)(1),
(2) Date: Jul. 25, 2019

(87) PCT Pub. No.: WO2018/139712
PCT Pub. Date: Aug. 2, 2018

(65) Prior Publication Data
US 2019/0389839 A1    Dec. 26, 2019

(30) Foreign Application Priority Data

Jan. 26, 2017    (KR) .................. 10-2017-0013010

(51) Int. Cl.
| | | |
|---|---|---|
| *C07D 401/14* | (2006.01) | |
| *G02F 1/155* | (2006.01) | |
| *G02F 1/1516* | (2019.01) | |
| *C09K 9/02* | (2006.01) | |
| *C07D 213/22* | (2006.01) | |

(52) U.S. Cl.
CPC .......... *G02F 1/1516* (2019.01); *C07D 213/22* (2013.01); *C07D 401/14* (2013.01); *C09K 9/02* (2013.01); *G02F 1/155* (2013.01); *C09K 2211/1029* (2013.01)

(58) Field of Classification Search
CPC ...... C07D 401/14; G02F 1/155; G02F 1/1516
See application file for complete search history.

(56) References Cited

U.S. PATENT DOCUMENTS

2003/0206326 A1* 11/2003 Berneth ............... G02F 1/1503
359/265

FOREIGN PATENT DOCUMENTS

| CN | 104292151 A | 1/2015 | |
|---|---|---|---|
| JP | 54-106083 A | 8/1979 | |
| JP | S58-4756 B2 | 1/1983 | |
| KR | 10-0832668 B1 | 5/2008 | |
| KR | 10-2011-0018628 A | 2/2011 | |
| KR | 10-2015-0144455 A | 12/2015 | |
| KR | 10-2016-0083236 A | 7/2016 | |
| WO | WO 2015/193301 A1 | 12/2015 | |
| WO | WO-2015193301 A1 * | 12/2015 | ............... C09K 9/02 |

OTHER PUBLICATIONS

Asaftei et al., "Novel Compounds with a Viologen Skeleton and N-Hetereocycles on the Peripheries: Electrochemical and Spectroscopic Properties," Helvetica Chimica Acta, vol. 94, 2011, pp. 1091-1101.
Asaftei et al., "Thermotropic ionic liquid crystals by molecular assembly and ion pairing of 4,4'-bipyridinium derivatives and tris(dodecyloxy)benzenesulfonates in a non-polar solvent," J. Mater. Chem., vol. 22, 2012, pp. 14426-14437.
Asaftei et al., "'Viologen' Dendrimers as Antiviral Agents: The Effect of Charge Number and Distance," J. Med. Chem., vol. 53, 2010, pp. 3480-3488.
Felderhoff et al., "Molecular Suppression of the Pimerization of Viologens (=4,4'-Bipyridinium Derivatives) Attached to Nanocrystalline Titanium Dioxide Thin-Film Electrodes," Helvetica Chimica Acta, vol. 83, 2000, pp. 181-192.
Guo et al., "Colorimetric Chemosensor for Barium Metal Ions Using Tris(bipyridinium-crown ether) Conjugate," Chem. Lett., vol. 42, 2013 (published online Feb. 2, 2013), pp. 194-196.
Rossensky et al., "Studies of tetra-(bipyridilium) salts as possible polyelectrochromic materials," Journal of Applied Electrochemistry, vol. 24, 1994, pp. 1213-1221.
Guo et al., "Colorimetric Chemosensor for Barium Metal ions Using Tris(bipyridinium-crown ether) Conjugate", Chemistry Letters, vol. 42, 2013, pp. 194-196.
Rossejnsky et al., "Studies of tetra-(bipyridilium) salts as possible polyelectrochromic materials", Journal of Applied Electrochemistry, vol. 24, 1994, pp. 1213-1221.

* cited by examiner

*Primary Examiner* — Bijan Ahvazi

(74) *Attorney, Agent, or Firm* — Birch, Stewart, Kolasch & Birch, LLP

(57) ABSTRACT

The present invention relates to an electrochromic compound, and an electrochromic composition and an electrochromic device, including the same. The electrochromic compound according to the present invention may achieve excellent black coloring effects and excellent curing characteristics, and thus may be used advantageously in an electrochromic device.

21 Claims, No Drawings

BLACK ELECTROCHROMIC COMPOUND, AND ELECTROLYTE-INTEGRATED RADIATION CURABLE ELECTROCHROMIC COMPOSITION AND ELECTROCHROMIC DEVICE WHICH CONTAIN SAME

CROSS REFERENCE TO RELATED APPLICATIONS

This application is the National Phase of PCT International Application No. PCT/KR2017/005011, filed on May 15, 2017, which claims priority under 35 U.S.C. 119(a) to Patent Application No. 10-2017-0013010, filed in Republic of Korea on Jan. 26, 2017, all of which are hereby expressly incorporated by reference into the present application.

TECHNICAL FIELD

The present invention relates to an electrochromic compound, and an electrochromic composition and an electrochromic device, including the same.

More particularly, the present invention relates to a viologen-based electrochromic compound having black electrochromic characteristics, and an electrolyte integrated photocurable electrochromic composition and an electrochromic device, including the same.

BACKGROUND ART

An electrochromic device (ECD) refers to an electrochemical device including one or more electrochromic materials that enable a chemical reaction capable of changing or adjusting a color to proceed as a result of an electrochemical reaction as electricity is applied to an oxidation or reduction electrode. Electrochromism is a well-known physical phenomenon observed for a specific class of compound that reversibly changes a color when a voltage is applied. This material undergoes a reversible change in optical characteristics by oxidation and reduction. Typically, an electrochromic material may be colorless when an electric field is not applied and may be colored when an electric field is applied.

Electrochromic materials may be divided into organic EC materials, inorganic EC materials, and organic-inorganic hybrid EC materials. Examples of a representative EC material include inorganic metal oxides such as tungsten oxide ($WO_3$), nickel oxide (NiO), and titanium oxide ($TiO_2$) and organic materials, such as bipyridinium (viologen) derivatives, quinone-based derivatives such as anthraquinone and azine-based derivatives such as phenothiazine.

Organic electrochromic materials are classified into oxidation color development types and reduction color development types. Examples of the oxidation color development types include phenylamine, polyaniline, fluoran, phenothiazine, and the like, and examples of the reduction color development types include viologen, anthraquinone, phthalic acid ester, and the like. Among these various organic electrochromic materials, the viologen derivatives have been recently actively studied due to advantages such as introduction of various substitution groups, driving at a low voltage, and stability of repeated driving (KR10-2011-0018628A).

Viologen-based electrochromic materials cause poor solubility due to the planarity of the structure thereof, production of a dimer of a viologen radical cation (V+) generated as a result of an electrochemical reaction in a reduction electrode, and the like. When the viologen-based electrochromic material is applied to the structure of the device, the poor solubility, the production of the dimer, and the like are recognized as causes of deterioration in stability for repeated driving.

The prior art technologies on black electrochromism usually uses simple mixing of a blue material and a green material, but in this case, it is difficult to satisfy a black coordinate required by a user, and it is likely to cause a color separation during a repeated driving.

Throughout the present specification, a plurality of documents are referenced, and citations thereof are indicated. The disclosure of each of the cited documents is incorporated herein by reference in its entirety to describe the level of the technical field to which the present invention pertains and the content of the present invention more apparently.

DISCLOSURE OF THE INVENTION

The present inventors have made efforts to provide a new electrochromic compound capable of providing an increased solubility in order to alleviate the molecular aggregation. As a result, unlike the existing mixing of blue and green electrochromic compounds, the present inventors synthesized a compound capable of providing black electrochromic characteristics as a single material, thereby completing the present invention.

Therefore, an object of the present invention is to provide an electrochromic compound which provides black electrochromic characteristics as a single material.

Another object of the present invention is to provide an electrochromic composition including the compound.

Still another object of the present invention is to provide an electrochromic device including the compound or the composition.

Yet another object of the present invention is to provide a method for preparing the electrochromic device.

Still yet another object of the present invention is to provide a product including the electrochromic device.

The other objects and advantages of the present invention will be more apparent from the following detailed description, claims and drawings of the invention.

To achieve these and other advantages and in accordance with the purpose of the present invention, as embodied and broadly described herein, there is provided a compound having the following Chemical Formula 1.

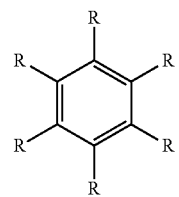

<Chemical Formula 1>

Here, R is each independently selected from the group consisting of hydrogen, a halogen, an alkyl, for example, a $C_1$-$C_{20}$ alkyl, a halogenated $C_1$-$C_{20}$ alkyl, an aryl group, an alkyl group linked to oxygen and nitrogen, an aryl group linked to oxygen and nitrogen, and a compound of the following Chemical Formula 2, with a proviso that at least three R's represent a compound of the following Chemical Formula 2.

<Chemical Formula 2>

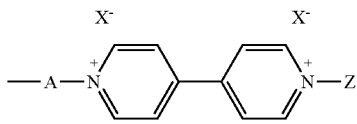

Here, X— represents a counter-anion.

Examples of the counter-anion include $AsF_6^-$, $SbF_6^-$, $TaF_6^-$, $ClO_4^-$, $CH_3SO_3^-$, $CF_3SO_3^-$, $C_4F_9SO_3^-$, $AlO_4$, $AlCl_4^-$, a halide, for example, $Cl^-$, $Br^-$, and $I^-$, $C(SO_2CF_3)_3^-$, a phosphate-substrate anion, for example, $PF_6^-$, $PF_3(CF_3)_3^-$, and $PF_4(C_2O_4)^-$, a borate-substrate anion, for example, $BF_4^-$, $B(C_2O_4)_2^-$, $BF_2(C_2O_4)^-$, $B(C_2O_4)(C_3O_4)^-$, $(C_2F_5BF_3)^-$, $B_{10}Cl_{10}^{2-}$, $B(C_6H_5)_4^-$, and $B_{12}F_{12}^{2-}$, a sulfonylimide-substrate anion, for example, $N(CF_3SO_2)_2^-$, $N(SO_2F)_2^-$, $N(C_2F_5SO_2)_2^-$, and $N(i\text{-}C_3F_7SO_2)_2^-$, and the like, but are not limited thereto.

Preferably, X may be one or more selected from the group consisting of $Cl^-$, $Br^-$, $I^-$, $F^-$, $ClO_4^-$, $BF_4^-$, $PF_6^-$, and $TFSi^-$, and in a specific exemplary embodiment, more improved driving characteristics may be exhibited by using $TFSi^-$.

A is a linker which links a molecule to benzene that is a central molecule, and A is not present or is each independently selected from the group consisting of a $C_1\text{-}C_{10}$ alkylene; a $C_1\text{-}C_{20}$ alkylene; a halogenated $C_1\text{-}C_{10}$ alkylene; a $C_2\text{-}C_{10}$ alkenylene; a $C_2\text{-}C_{20}$ alkenylene; a halogenated $C_2\text{-}C_{10}$ alkenylene; a $C_2\text{-}C_{10}$ alkynylene; a $C_2\text{-}C_{20}$ alkynylene; a halogenated $C_2\text{-}C_{10}$ alkynylene; and a heteroatom selected from N, P, O, and S, and each of them may also be substituted with one or more selected from the group consisting of a 3- to 10-membered ring cycloalkyl; a 3- to 10-membered ring heterocycloalkyl including a heteroatom selected from N, P, O, and S; a $C_{6\text{-}40}$ aryl; a $C_1\text{-}C_{20}$ alkyl; a halogen, a hydroxyl, and CN.

Z is a color regulator which adjusts a discoloration color, and may be each independently selected from the group consisting of a $C_1\text{-}C_{20}$ alkyl; a $C_1\text{-}C_{20}$ alkyl substituted with CN; a $C_1\text{-}C_{20}$ alkoxy; CN; a $C_{2\text{-}20}$ alkenyl; a $C_{2\text{-}20}$ alkynyl; a 3- to 10-membered ring cycloalkyl; a 3- to 10-membered ring heterocycloalkyl including a heteroatom selected from N, P, O, and S; a $C_{6\text{-}40}$ aryl; a $C_{6\text{-}40}$ aryl substituted with one or more substitution groups selected from a $C_1\text{-}C_{20}$ alkyl, a $C_1\text{-}C_{20}$ alkoxy, a $C_1\text{-}C_{20}$ aryloxy, a halogen, a hydroxyl, and CN; and a $C_{6\text{-}40}$ heteroaryl including a heteroatom selected from N, P, O, and S.

According to an exemplary embodiment of the present invention, the three compounds represented by Chemical Formula 2 are substituted at any position of the benzene represented by Chemical Formula 1, and may be preferably substituted at the 1, 3, and 5 positions of the benzene, and in this case, the remaining R's may be independently selected from hydrogen, a halogen, an alkyl group, an aryl group, an alkyl group linked to oxygen and nitrogen, an aryl group, and the like, and may be preferably hydrogen or a $C_1\text{-}C_{20}$ alkyl group.

According to another exemplary embodiment of the present invention, the three R's positioned at the Nos. 1, 3, and 5 of Chemical Formula 1 are each independently the compound of Chemical Formula 2, and among them, one R or two R's may be $R_a$ in which Z is independently selected from the group consisting of a $C_1\text{-}C_{20}$ alkyl; a $C_1\text{-}C_{20}$ alkyl substituted with CN; a $C_1\text{-}C_{20}$ alkoxy; CN; a $C_{2\text{-}20}$ alkenyl; a $C_{2\text{-}20}$ alkynyl; a 3- to 10-membered ring cycloalkyl; and a 3- to 10-membered ring heterocycloalkyl including a heteroatom selected from N, P, O, and S, in Chemical Formula 2, and the remaining two R's or one R may be $R_b$ in which Z is independently selected from the group consisting of a $C_{6\text{-}40}$ aryl; a $C_{6\text{-}40}$ aryl substituted with one or more substitution groups selected from a $C_1\text{-}C_{20}$ alkyl, a $C_1\text{-}C_{20}$ alkoxy, a $C_1\text{-}C_{20}$ aryloxy, a halogen, a hydroxyl, and CN; and a $C_{6\text{-}40}$ heteroaryl including a heteroatom selected from N, P, O, and S, in Chemical Formula 2.

As described above, $R_a$ containing Z selected from the group consisting of a $C_1\text{-}C_{20}$ alkyl; a $C_1\text{-}C_{20}$ alkyl substituted with CN; a $C_1\text{-}C_{20}$ alkoxy; CN; a $C_{2\text{-}20}$ alkenyl; a $C_{2\text{-}20}$ alkynyl; a 3- to 10-membered ring cycloalkyl; and a 3- to 10-membered ring heterocycloalkyl including a heteroatom selected from N, P, O, and S finally achieves a blue-based electrochromism at a wavelength of 410 to 495 nm, whereas as described above, $R_b$ containing Z selected from the group consisting of a $C_{06}\text{-}40$ aryl; a 06-40 aryl substituted with one or more substitution groups selected from a $C_1\text{-}C_{20}$ alkyl, a $C_1\text{-}C_{20}$ alkoxy, a $C_1\text{-}C_{20}$ aryloxy, a halogen, a hydroxyl, and CN; and a $C_{6\text{-}40}$ heteroaryl including a heteroatom selected from N, P, O, and S finally achieves a green-based electrochromism at a wavelength of 495 to 590 nm.

According to still another exemplary embodiment of the present invention, the three R's positioned at the Nos. 1, 3, and 5 of Chemical Formula 1 are each independently the compound of Chemical Formula 2, and among them, one R or two R's may be $R_a$ in which Z exhibits a blue-based elecrochromism, in Chemical Formula 2, and the remaining two R's or one R may be $R_b$ in which Z exhibits a green-based electrochromism, in Chemical Formula 2.

The electrochromic compound substituted with at least three or more R's may be characterized by finally achieving black electrochromism by each independently substituting a viologen substituent including $R_a$ and $R_b$ according to a specific ratio.

The viologen substituent including both $R_a$ and $R_b$ may be substituted regardless of at least three or more positions of a benzene, and may be most preferably substituted at the 1, 3, and 5 positions of the benzene.

In an exemplary embodiment, $R_b$ may be a $C_{6\text{-}40}$ aryl having any one of the following structures:

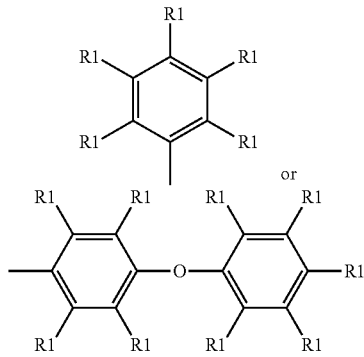

Here, R1 may be each independently selected from the group consisting of hydrogen, a halogen, a $C_1\text{-}C_{10}$ alkyl, CN, a hydroxyl, and a $C_1\text{-}C_{10}$ alkoxy.

According to another exemplary embodiment of the present invention, the compound having Chemical Formula 1 may be represented by the following chemical formula.

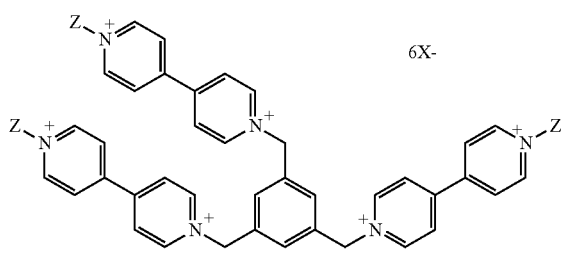

Here, X— is a counter anion, and a halogen-based anion, $PF_6^-$, $BF_4^-$, and the like may be usually used, and in an exemplary embodiment, an improvement in solubility and stability, and the like may be induced by using $TFSi^-$.

Z is each independently a substituent of viologen and serves to adjust a discoloration color, and it is possible perform blue or green driving according to the type of Z. Typically, the blue color and the green color can be implemented by introducing an alkyl derivative and an aryl derivative, respectively, and a more detailed content is the same as that previously described in detail.

In a preferred exemplary embodiment, Z is characterized by not including an anchoring group. The anchoring group is understood to denote a group capable of mediating an electrochromic material to be bonded to another surface, and specifically, the anchoring group means not including an anchoring group selected from, for example, $-PO_4(R')_2$, $-PO_2HRb$ (here, $R_b$ is selected from an alkyl group or an aryl group), $-SO_3H$, $-CONHOH$, $-NO_2$, $-COOH$, $-P(O)(OR')_2$ (here, R' is independently selected from the group consisting of hydrogen and an alkyl group), $-P(=O)(R_a)(OH)$ (here, $R_a$ is selected from the group consisting of an arbitrarily branched $C_1$-$C_{18}$ alkyl group, an arbitrarily substituted $C_5$-$C_{12}$ aryl group, and a halogenated derivative thereof), $-PO_4(R')_2$, $-PO_2HRb$ (here, Rb is selected from an alkyl group or an aryl group), $-SO_3H$, $-CONHOH$, $-NO_2$, acetylacetonate, acrylic acid derivatives, malonic acid derivatives, rhodanine-3-acetic acid, propionic acid, salicylic acid, formic acid anhydride, and the like.

Another aspect of the present invention is to provide an electrochromic composition including the compound (an integrated black electrochromic material) of the present invention.

Electrolyte Integrated Black Electrochromic Material

The details on an electrolyte integrated black electrochromic material included in the composition of the present invention are the same as those described above.

Toning Agent

In an exemplary embodiment, the electrochromic composition of the present invention may be an electrochromic composition including the electrolyte integrated black electrochromic material of the present invention as a first cathodic electrochromic material and further including a compound represented by the following Chemical Formula 1 as a second cathodic electrochromic material.

<Chemical Formula 1>

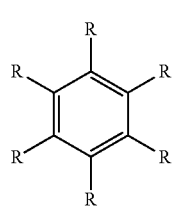

Here, R is each independently selected from the group consisting of hydrogen, a halogen, an alkyl, for example, a $C_1$-$C_{20}$ alkyl, a halogenated $C_1$-$C_{20}$ alkyl, an aryl group, an alkyl group linked to oxygen and nitrogen, an aryl group linked to oxygen and nitrogen, and a compound of the following Chemical Formula 2, with a proviso that at least three R's represent a compound of the following Chemical Formula 2.

<Chemical Formula 2>

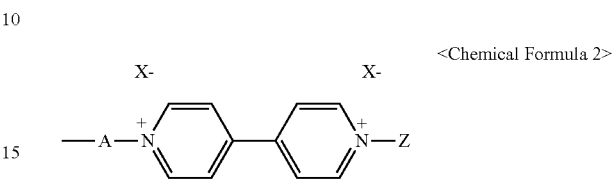

Here, X— represents a counter-anion.

Examples of the counter-anion include $AsF_6^-$, $SbF_6^-$, $TaF_6^-$, $ClO_4^-$, $CH_3SO_3^-$, $CF_3SO_3^-$, $C_4F_9SO_3^-$, $AlO_4^-$, $AlCl_4^-$, a halide, for example, $Cl^-$, $Br^-$, and $I^-$, $C(SO_2CF_3)_3^-$, a phosphate-substrate anion, for example, $PF_6^-$, $PF_3(CF_3)_3^-$, and $PF_4(C_2O_4)^-$, a borate-substrate anion, for example, $BF_4^-$, $B(C_2O_4)_2^-$, $BF_2(C_2O_4)^-$, $B(C_2O_4)(C_3O_4)^-$, $(C_2F_5BF_3)^-$, $B_{10}Cl_{10}^{2-}$, $B(C_6H_5)_4^-$, and $B_{12}F_{12}^{2-}$, a sulfonylimide-substrate anion, for example, $N(CF_3SO_2)_2^-$, $N(SO_2F)_{2-}$, $N(C_2F_5SO_2)_2^-$, and $N(i$-$C_3F_7SO_2)_2^-$, and the like, but are not limited thereto.

Preferably, X may be one or more selected from the group consisting of $Cl^-$, $Br^-$, $I^-$, $F^-$, $ClO_4^-$, $BF_4^-$, $PF_6^-$, and $TFSi^-$, and in a specific exemplary embodiment, more improved driving characteristics may be exhibited by using $TFSi^-$.

A is a linker which links a molecule to a benzene that is a central molecule, and is each independently selected from a $C_1$-$C_{20}$ alkylene; a $C_2$-$C_{20}$ alkenylene; and a $C_2$-$C_{20}$ alkynylene, and each of them contains, therein, or is substituted with, one or more selected from the group consisting of a 3- to 10-membered ring cycloalkyl; a 3- to 10-membered ring heterocycloalkyl including a heteroatom selected from N, P, O, and S; a $C_{6-40}$ aryl; a $C_1$-$C_{20}$ alkyl; a $C_1$-$C_{20}$ alkyl linked to a heteroatom selected from N, P, O, and S; a 3- to 10-membered cycloalkyl; a 3- to 10-membered ring heterocycloalkyl including a heteroatom selected from N, P, O, and S; a $C_{6-40}$ aryl; and a halogen, a hydroxyl, CN, and a combination thereof.

Z is each independently selected from a $C_1$-$C_{20}$ alkyl; a $C_{2-20}$ alkenyl; a $C_{2-20}$ alkynyl; a 3- to 10-membered ring cycloalkyl; a 3- to 10-membered ring heterocycloalkyl including a heteroatom selected from N, P, O, and S, and each of them contains, therein, or is substituted with, one or more selected from the group consisting of a $C_{6-40}$ aryl; a $C_1$-$C_{20}$ alkyl; a $C_1$-$C_{20}$ alkyl linked to a heteroatom selected from N, P, O, and S; a 3- to 10-membered ring heterocycloalkyl including a heteroatom selected from N, P, O, and S; a $C_{6-40}$ aryl; and a halogen, a hydroxyl, CN, and a combination thereof.

The second cathodic material contains at least two or more R's, and is most preferably a material in which Nos. 1 and 2 positions or Nos. 1, 2, 4, and 5 positions of a benzene are substituted.

According to an exemplary embodiment, the second cathodic material may be a compound represented by the following chemical formula.

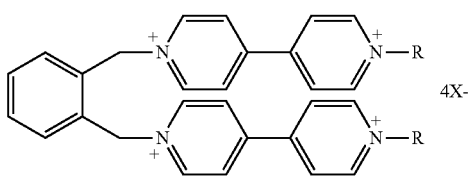

Here, X— represents a counter-anion,

R is independently selected from the group consisting of a $C_1$-$C_{20}$ alkyl, a $C_1$-$C_{20}$ alkyl substituted with a $C_6$-$C_{40}$ aryl, benzyl, a 3- to 10-membered ring heterocycloalkyl including a heteroatom, a $C_{6-40}$ aryl, and a $C_{6-40}$ aryl substituted with a $C_1$-$C_{20}$ alkyl; and a $C_{6-40}$ heteroaryl including a heteroatom selected from N, P, O, and S, and the second cathodic electrochromic material has discoloration characteristics in which Y is 0.93 to 1.04, L* is 8.35 to 9.35, a* is 41.03 to 46.17, and b* is −23.38 to −24.92 in the color coordinate.

The L*a*b* color space is defined based on studies on the human eyesight, particularly the L value which is the luminance axis is designed so as to correspond to the brightness felt by a human being. The color region of the Lab color space is much larger than the color region which can be perceived by a human, so that a color implemented by a display device can be expressed with more precise values.

In the L*a*b* color space, the L* value indicates the brightness. L*=0 indicates absolute black, and L*=100 indicates absolute white. Human eyes recognize L* 30 or less as black. a* indicates whether to be biased toward red or green. If a* is a negative number, a* indicates a color that is biased towards green, and if a* is a positive number, a* indicates a color that is biased towards red/violet. b* indicates yellow and blue. If b* is a negative number, b* indicates blue, and if b* is a positive number, b* indicates yellow.

The second cathodic electrochromic material is a viologen-based compound which is characterized by a red-based color development, and when the viologen-based compound is used as a toning agent together with the integrated black electrochromic material, it is possible to implement a color development closer to black.

According to another exemplary embodiment, the second cathodic material may be represented by the following chemical formula.

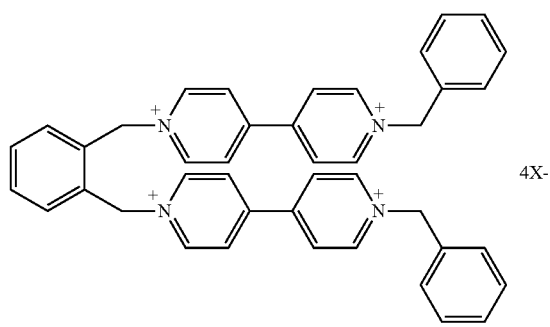

(X⁻ represents a counter anion).

As described above, when the composition of the present invention includes first and second cathodic electrochromic materials in order to implement a color development closer to black, a molar ratio of the first cathodic electrochromic material: the second cathodic electrochromic material may be 1:1 to 500:1, 2:1 to 100:1, or 3:1 to 50:1, preferably 5:1 to 10:1.

Counter Oxidation Material

The electrochromic composition of the present invention may further include a counter oxidation compound.

The counter oxidation compound included in the composition of the present invention is not limited to a specific example. The counter oxidation compound need not be an electrochromic compound, and may be at least selected from the compounds having the following characteristics. When the counter oxidation compound is also an electrochromic compound, the counter oxidation compound needs to have low absorbance for visible light in a bleached state, have good stability against oxygen, and exhibit good solubility in typical electrochromic solvents.

As the counter oxidation compound, it is possible to exemplify ferrocene and various ferrocene-based compounds, for example, compounds selected from ethyl ferrocene, propyl ferrocene, t-butyl ferrocene, a $C_1$-$C_{20}$ alkyl ferrocene or a halogenated ferrocene; compounds selected from amine-based compounds, for example, phenoxazine, 5,10-dihydrophenazine, N, N, N',N'-tetramethyl-p-phenylenediamine, phenothiazine, 10-methylphenothiazine, and isopropyl phenothiazine; or sulfur compounds, for example, compounds selected from thianthrene or tetrathiafulvalene; and the like, but the counter oxidation compound is not limited thereto Solvent As an appropriate solvent, it is possible to use a redox-inert material that does not react with the electrochromic material of the composition.

The appropriate solvent may be one or more selected from, for example, ethylene carbonate, propylene carbonate, gamma butyrolactone, gamma-valerolactone, acetonitrile, propionitrile, benzonitrile, glutaronitrile, methylglutaronitrile, dimethylformamide, N-methylpyrrolidone, sulfolane, 3-methyl sulfolane, benzene, toluene, methyl ethyl ketone, acetone, ethanol, tetrahydrofurfuryl alcohol, 2-methoxyethyl ether, xylene, cyclohexane, 3-methylcyclohexane, ethyl acetate, ethyl phenylacetate, tetrahydrofuran, methanol, methyl propionate, ethylene glycol, ethylene carbonate, an ionic liquid, and mixtures thereof, but is not limited thereto.

Electrolyte Material

In another exemplary embodiment, the composition of the present invention may further include an electrolyte material.

The electrolyte material needs to be compatible with other components, and in particular, the electrolyte material need not be reactive with an electrochromic material.

Examples of the electrolyte material include alkali metal salts, for example, sodium salt, lithium salt, bis(trifluoromethane)sulfonimide lithium salt, tetraalkylammonium salt, aluminum chloride, aluminum boride, persulfates, bis(fluorosulfonyl)imide, or the like, but are not limited thereto.

Curing Agent or Gelling Agent

In still another exemplary embodiment, the electrochromic composition of the present invention may further include other additives such as a curing agent or a gelling agent.

The curing agent or the gelling agent needs to be non-reactive with another component, is electrochromically stable, and need not remarkably reduce conductivity of an electrochromic composition.

Examples of the curing agent or the gelling agent include an acrylic polymer, polyacrylate, polymethylmethacrylate, polyvinyl acetate, polyurethane, polystyrene, polyacetonitrile, cellulose, carboxymethyl cellulose, hydroxymethyl cellulose, cellulose propionate, hydroxypropylmethyl cellulose, gum, hydrochloride, gellan, carrageenan, pullulan, polyethylene oxide, polypropylene oxide, polyvinyl acetate, poly(N-vinyl pyrrolidone), polyvinylidene fluoride, or the like, but are not limited thereto.

The concentration of the curing agent or the gelling agent may vary depending on the characteristics of the curing agent and the viscosity required for the electrochromic composition. In an exemplary embodiment, the concentration of the curing agent or the gelling agent may be 1 to 50 wt %, 1 to 30 wt %, 3 to 20 wt %, or 5 to 15 wt % of the entire electrochromic composition, but is not limited thereto.

UV Stabilizer to Antioxidant

In yet another exemplary embodiment, the electrochromic composition of the present invention may further include other additives such as a UV stabilizer to an antioxidant.

The UV stabilizer or the antioxidant is for protecting electrochromic materials from ultraviolet rays by absorbing UV rays (<350 nm), and may be used without limitation as long as the UV stabilizer or the antioxidant is a material having UV absorbing power.

Examples of the UV stabilizer to the antioxidant include 2,4-dihydroxybenzophenone (UVINUL® 3000, BASF), 2-hydroxy-4-n-octyloxybenzophenone (SANDUVOR® 3035, Clariant), 2-(2H-benzotriazol-2-yl)-6-dodecyl-4-methylphenol (Tinuvin® 571, Ciba), 2,2'-dihydroxy-4-methoxy-benzophenone (Cyasorb 24™, American Cyanamid Company), ethyl 2-cyano-3,3-diphenylacrylate (UVINUL® 3035, BASF), 2-ethylhexyl 2-cyano-3,3-diphenyl-acrylate (UVINUL® 3039, BASF), 2-ethylhexyl p-methoxycinnamate (UVINUL® 3088, BASF), 2-hydroxy-4-methoxy-benzophenone (CHIMASSORB® 90, Ciba), dimethyl 4-methoxybenzylidene malonate (SANDUVOR® PR-25, Clariant), and the like, but are not limited thereto.

In an exemplary embodiment, the electrochromic compound of the present invention may include a viologene-containing electrochromic material at 20 to 140 mM, a counter material at 20 to 160 mM, and an electrolyte material at 0.5 to 1.4 M. Further, the electrochromic compound of the present invention may include a 5 to 40% curing composition solution and a UV stabilizer to an oxidant in an amount of 1 to 20 wt %.

Still another aspect of the present invention provides an electrochromic device (EDC) including the above-described compound of the present invention (an integrated black electrochromic material) or the above-described composition of the present invention.

The electrochromic device of the present invention may include a first substrate provided with a first electrode and a second substrate provided with a second electrode, in which the compound or the composition may be included in a space between the two substrates disposed spaced apart from each other.

A typical ECD structure includes a first transparent electrode laminated on a first substrate (for example, glass or plastic), a second transparent electrode facing the first transparent electrode and laminated on the other substrate, an electrochromic layer including an electrochromic material between the two electrodes, an electrolyte layer (a liquid, a solid, or a gel), and any counter electrode layer.

The electrochromic device may be manufactured by a method including the steps of (i) preparing an electrochromic solution including: the electrochromic compound of the present invention (first cathodic and second cathodic compounds); a counter oxidation compound selected from a ferrocene-based compound or an amine-based compound; and a curing agent; (ii) preparing a cell including a first substrate provided with a first electrode and a second substrate provided with a second electrode, in which the two substrates are disposed spaced apart from each other; (iii) injecting the prepared electrochromic solution into a space between the first substrate and the second substrate of the cell; and (iv) curing the injected solution.

In a preferred exemplary embodiment, the integrated electrochromic compound having black electrochromic characteristics of the present invention is characterized by enabling the electrochromic material on a highly viscous gel obtained in step (iv) to freely diffuse by not including an anchoring group in a substituting group represented by Z. When an anchoring group is included in a substitution group, due to strong hydrogen bond characteristics of the anchoring group, deterioration in electrode characteristics caused by interaction with an electrode, reduction in diffusion rate caused by an intermolecular hydrogen bond, and the like are caused in a device using diffusion of an electrochromic material in a solution, and consequently, these are mainly responsible for deterioration in driving characteristics of the electrochromic device.

Yet another aspect of the present invention provides a product including the electrochromic device. Examples of a field to which the electrochromic device is applied include electrochromic mirror for an automobile, window glass for construction, smart window, a transparent display, a reflective-type display, an electronic shelf label (ESL), and the like, and it is predicted that the scale of the world market driven by the electrochromic technology continuously exhibits a great growth momentum due to the demand of the age for energy saving and safety.

The electrochromic compound according to the present invention may achieve excellent black coloring effects and excellent curing characteristics, and thus may be used advantageously in an electrochromic device.

MODES FOR CARRYING OUT THE PREFERRED EMBODIMENTS

Reference will now be made in detail to the preferred embodiments of the present invention, examples of which are illustrated in the accompanying drawings. It will also be apparent to those skilled in the art that various modifications and variations can be made in the present invention without departing from the spirit or scope of the invention. Thus, it is intended that the present invention cover modifications and variations of this invention provided they come within the scope of the appended claims and their equivalents.

Description will now be given in detail of a drain device and a refrigerator having the same according to an embodiment, with reference to the accompanying drawings.

Hereinafter, the present invention will be described in more detail through the Examples. These Examples are provided only for more specifically describing the present invention, and it will be obvious to a person with ordinary skill in the art to which the present invention pertains that the scope of the present invention is not limited by these Examples.

EXAMPLES

I. Preparation Example

1. Synthesis of First Cathodic Electrochromic Material (Containing Viologen)

A first cathodic electrochromic material containing viologen may be prepared through the steps such as the following reaction formulae.

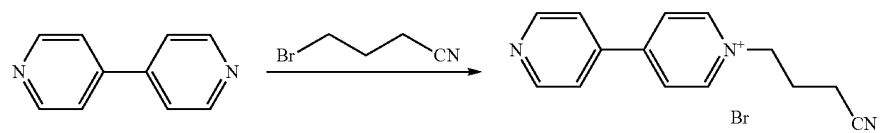
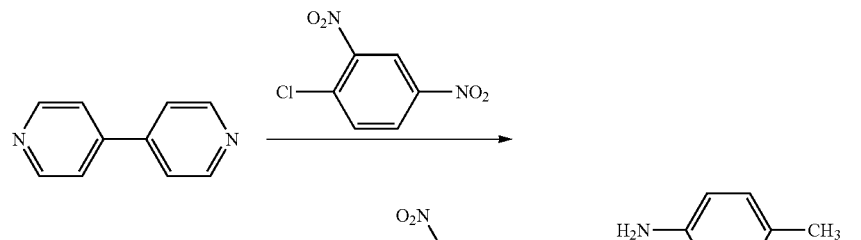
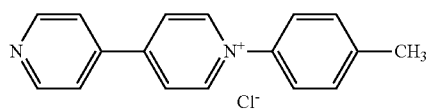
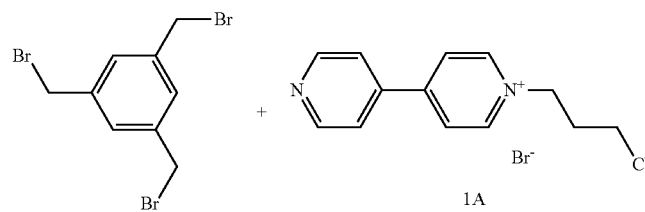
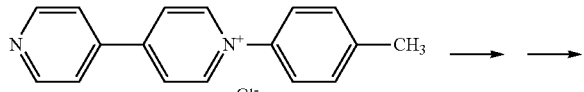
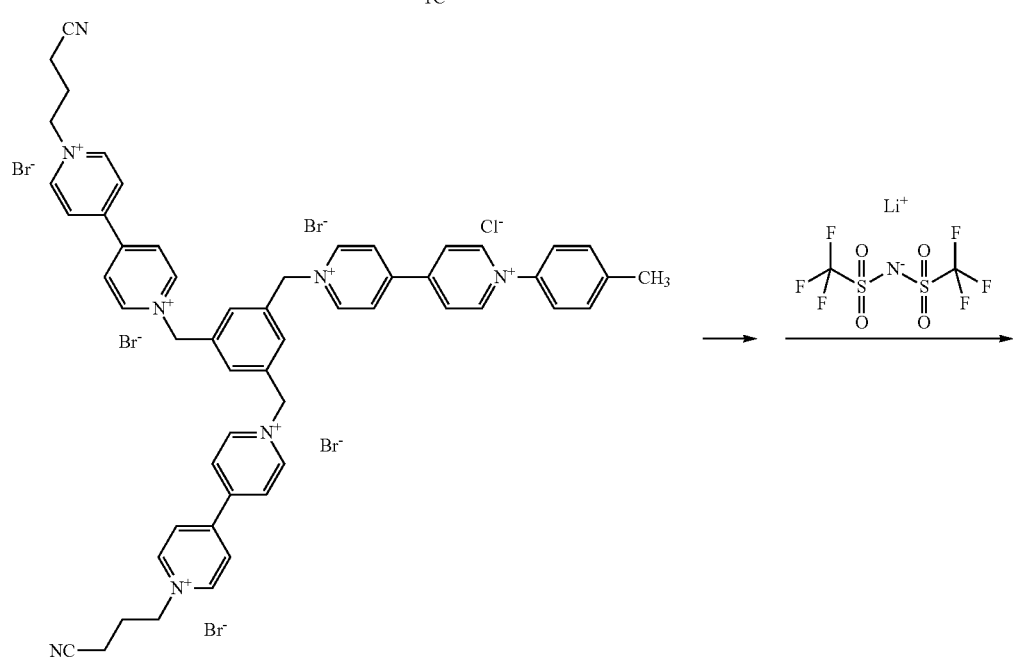

-continued

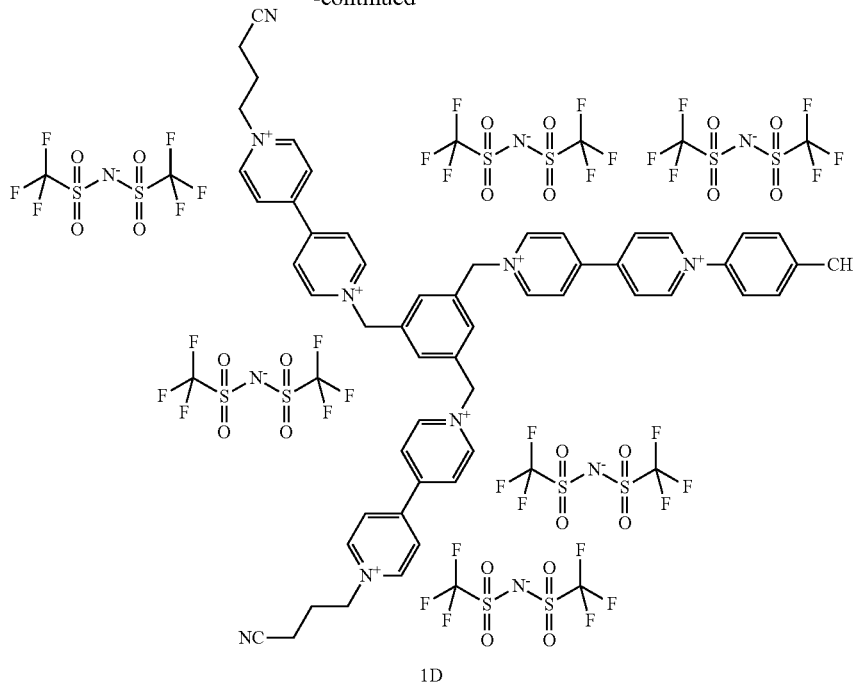

1D (1) Synthesis of Compound of Chemical Formula 1A

[Chemical Formula 1A]

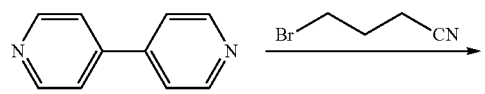

12.7 g of 4,4'-bipyridyl and 10.0 g of 4-bromobutyronitrile were refluxed in 50 ml of acetonitrile for a day. A precipitate was left behind by filtering the mixture, and the filtered liquid was refluxed again. A yellow solid, which is a precipitate, was stirred in 200 ml of acetone and filtered. The reflux and filtration process was repeated three times. The yellow precipitate was all collected, washed with acetone, and dried at normal temperature under reduced pressure. A compound of Chemical Formula 1A at a yield of 64% was obtained.

[Reaction Formula 1A]

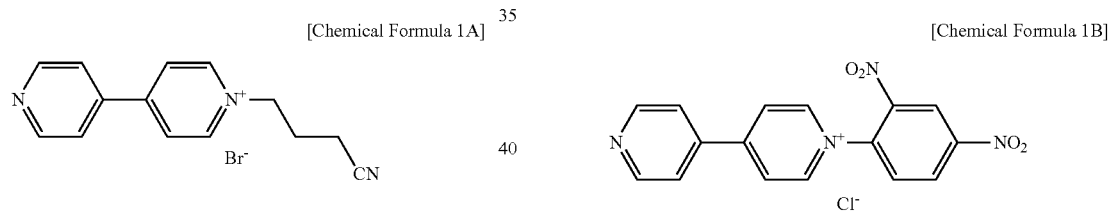

(2) Synthesis of Compound of Chemical Formula 1B

[Chemical Formula 1B]

9.2 g of 4,4'-bipyridyl and 10.0 g of 1-chloro-2,4-dinitrobenzene were refluxed in 50 ml of acetonitrile for 3 days. Subsequently, a yellow residue was filtered, and the filtrate was refluxed again. An obtained yellow solid was stirred in 500 ml of acetone and filtered. The reflux process was repeated three times. Precipitates obtained through the repeated reflux and filtration were washed several times with acetone. Subsequently, a compound of Chemical Formula 1A was obtained by drying the precipitate at a temperature of 100° C. in an oven, and the yield thereof was 70%.

[Reaction Formula 1B]

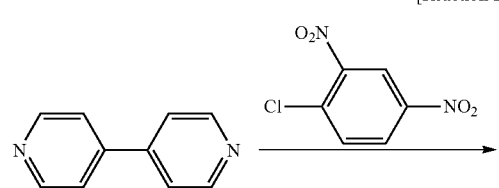

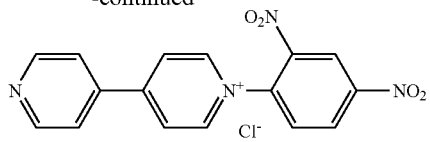

(3) Synthesis of Compound of Chemical Formula 1C

[Chemical Formula 1C]

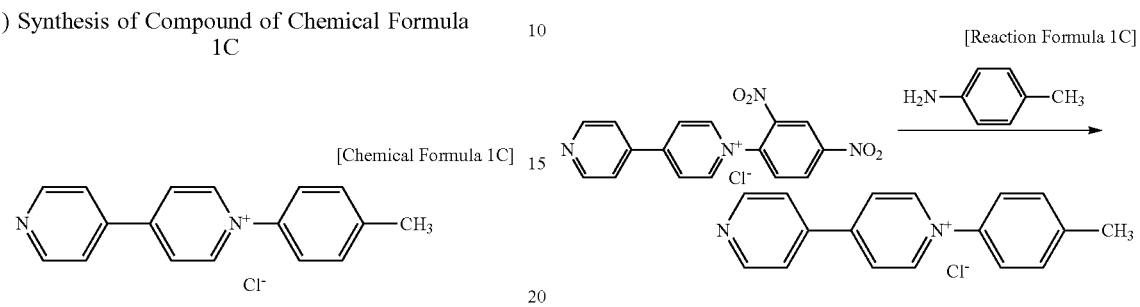

20.0 g of the compound of Chemical Formula 1B and 17.8 g of para-toluidine were refluxed in 500 ml of ethyl alcohol for 3 days. A precipitate was filtered, and a filtered solution was refluxed again. A yellow precipitate was stirred in 500 ml of acetone and filtered, and the reflux process was repeated twice. The filtered precipitate was washed several times with acetone. Subsequently, a compound of Chemical Formula 1C was obtained by drying the precipitate at a temperature of 100° C. in an oven, and the yield thereof was 89%.

[Reaction Formula 1C]

(4) Synthesis of Compound of Chemical Formula 1D

[Chemical Formula 1D]

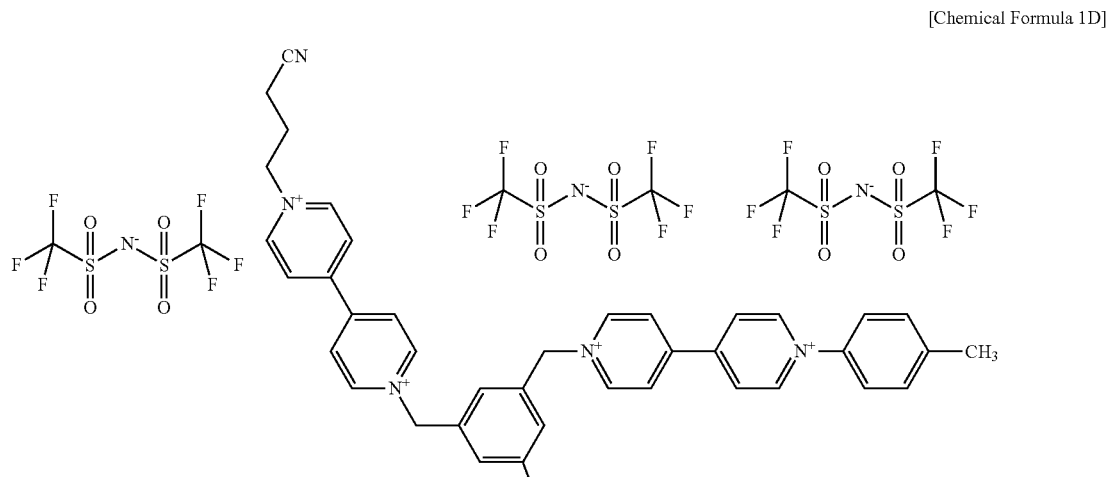

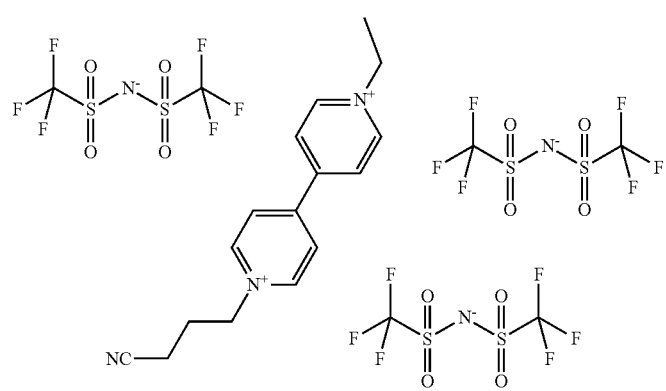

3.0 g of 1,3,5-trisbromomethylbenzene, 10.8 g of the compound of Chemical Formula 1A, and 5 g of the compound of Chemical Formula 1C were refluxed in 300 ml of methanol for 5 days. Subsequently, a dark brown solid obtained after removing the solvent was dried. The compound obtained above and 42 g of bis(trifluoromethane) sulfonimide lithium salt were dissolved in 400 ml of distilled water and mixed. Subsequently, a solid obtained by filtering the reactant liquid was dissolved in acetonitrile and dried by using $MgSO_4$. A compound of Chemical Formula 1D was obtained by vacuum-drying a solid obtained through concentration under reduced pressure, and the yield thereof was 70%.

[Reaction Formula 1D]

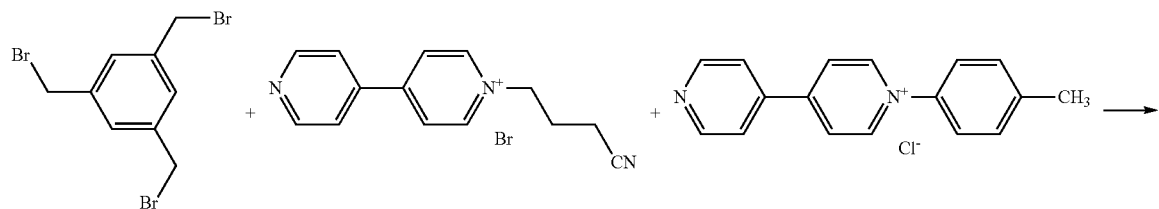

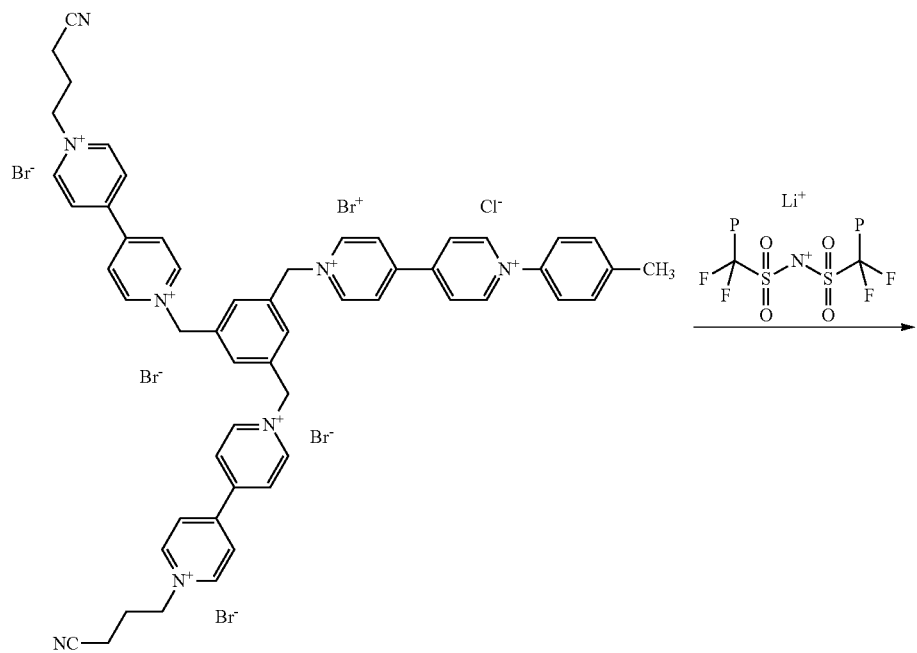

-continued
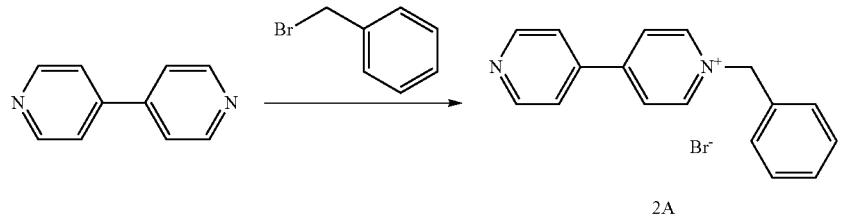
2. Synthesis of Second Cathodic Electrochromic Material (Toning Agent)
A second cathodic electrochromic material containing viologen may be prepared through the steps such as the following reaction formulae.
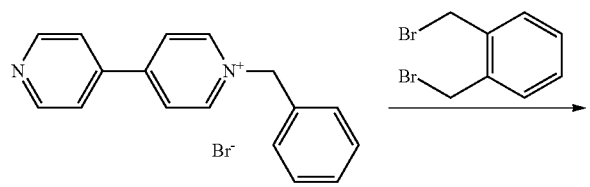
2A
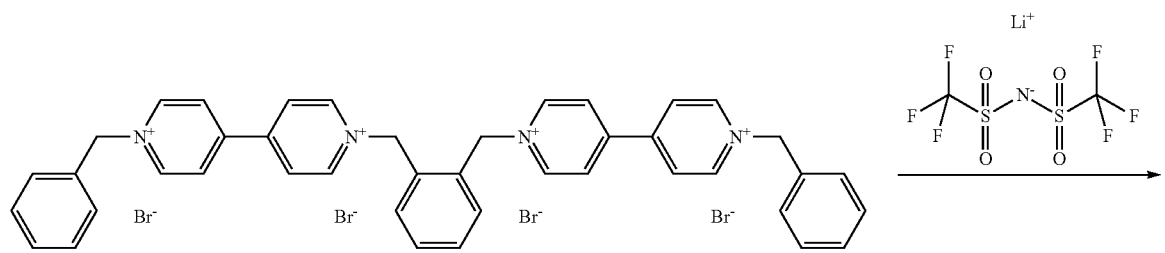

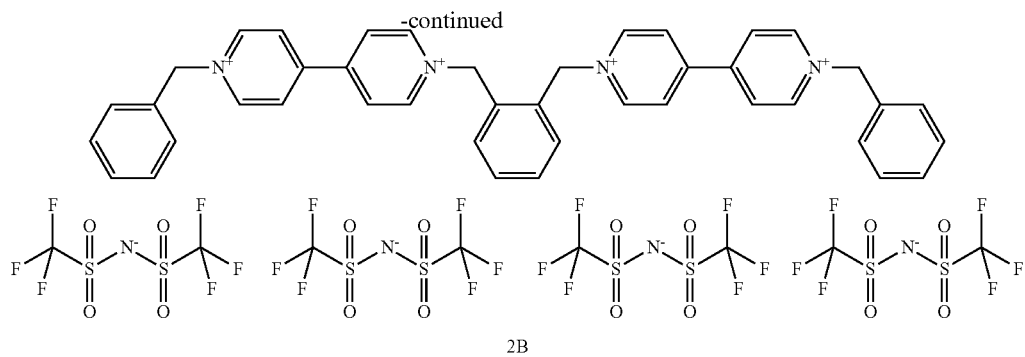

2B (1) Synthesis of Compound of Chemical Formula 2A

[Chemical Formula 2A]

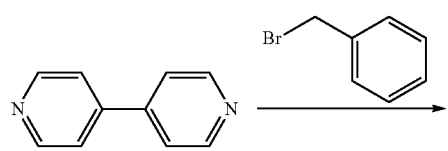

10.0 g of 4,4'-bipyridyl and 9.9 g of benzyl bromide were stirred in 150 ml of acetone at 50° C. for 3 days, subsequently, a yellow precipitate was filtered, and the filtered solution was stirred again. The stirring and filtration process was repeated three times. A yellow precipitate obtained after the filtration was stirred in 500 ml of acetone and filtered. Subsequently, the precipitate was filtered and washed several times with acetone. Subsequently, a compound of Chemical Formula 2A was obtained by drying the precipitate at a temperature of 70° C. in an oven, and the yield thereof was 75%.

[Reaction Formula 2A]

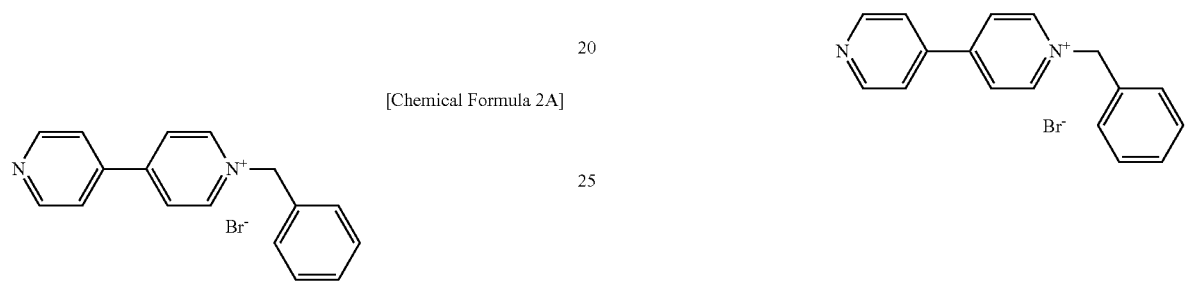

(2) Synthesis of Compound of Chemical Formula 2B

[Chemical Formula 2B]

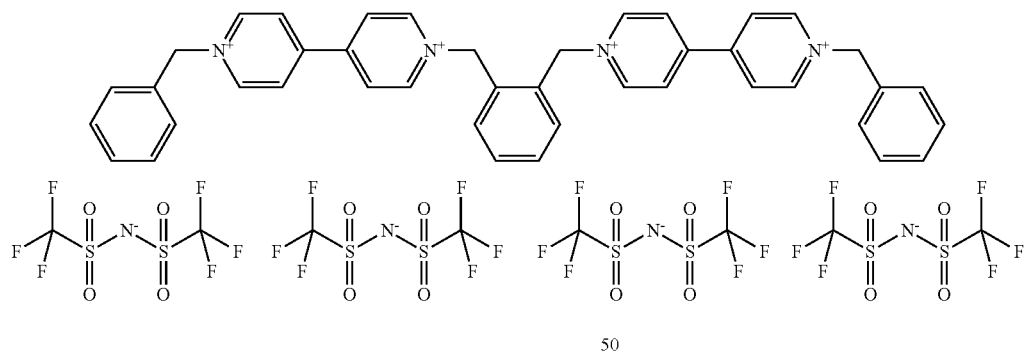

5.0 g of 1,2-bisbromomethyl benzene and 27 g of the compound of Chemical Formula 2A were refluxed in 100 ml of methanol for 3 days. Subsequently, a pale yellow solid obtained after removing the solvent was dried. The compound obtained above and 37 g of bis(trifluoromethane) sulfonimide lithium salt were dissolved in 400 ml of distilled water, and then mixed. Subsequently, a solid obtained by filtering the reactant liquid was dissolved in acetonitrile and the solution was dried by using $MgSO_4$. A compound of Chemical Formula 2B was obtained by vacuum-drying a solid obtained through concentration under reduced pressure, and the yield thereof was 68%.

[Reaction Formula 2B]

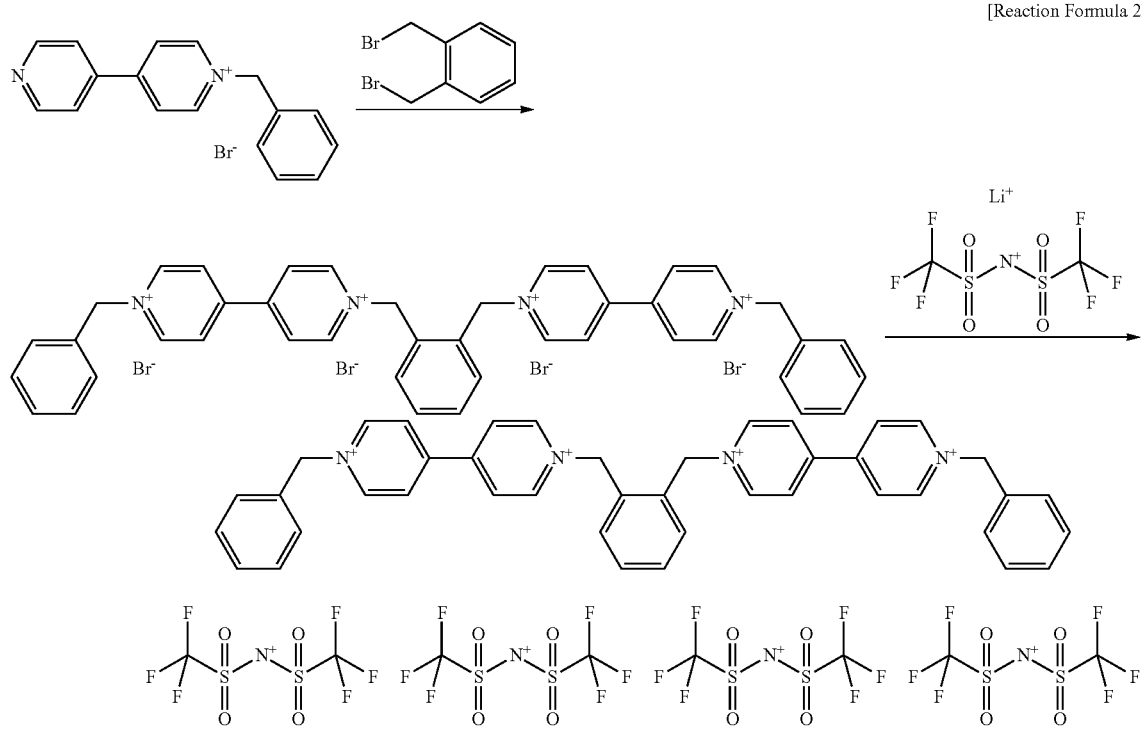

3. Preparation of Black Electrochromic Composition

A Solution:

Viologen and ferrocene of the prepared first cathodic electrochromic material (Chemical Formula 1D) were dissolved at a concentration of 49 mM and 146 mM, respectively in propylene carbonate (PC). 7 g of the corresponding solution and 3 g of a photocurable gel electrolyte (LiTFSi 1.4 M, curing composition 40 wt %) were mixed and appropriately stirred.

B Solution:

Viologen and ferrocene of the prepared second cathodic electrochromic material (Chemical Formula 2B) were dissolved at a concentration of 73 mM and 146 mM, respectively in PC. 7 g of the corresponding solution and 3 g of a photocurable gel electrolyte (LiTFSi 1.4 M, curing composition 40 wt %) were mixed and appropriately stirred.

4. Manufacture of Device

A cell was manufactured by joining two sheets of ITO glass with a size of 50×50 mm, such that the ITO surfaces face each other so as to maintain a space gap of 240 μm. After the A Solution and a mixed solution of A+B (A/B=88/12) were injected into the cell, the injection port was clogged, and the solutions were cured by exposing the cell at 2,000 mJ/m².

II. Experimental Example

1. Electrochromic Characteristics

(1) Example

The black specifications to be currently developed in the field to which the present invention pertains are Y: 1% or less, L*<32+3, a*: −4±1, and b*: 1±1, and in the present experimental example, the degree of electrochromism was measured by using the manufactured cell. Specifically, after a 1.5 V DC voltage was applied to the cell by using a DC power supply, the transmittance was measured by using a spectrometer in order to confirm the degree of electrochromism, and the results thereof are shown in the following Table 1.

TABLE 1

|  | Y | L* | a* | b* |
| --- | --- | --- | --- | --- |
| A | 1.27 | 11.09 | −13.83 | 7.47 |
| A/B = 88/12 | 0.78 | 7.00 | −4.20 | 0.46 |

As a result of the experiment, it was confirmed that even when only the first cathodic electrochromic material was included, the black coordinate was satisfied, and it was confirmed that when the second cathodic electrochromic material was mixed with the first cathodic electrochromic material, all the black specifications required in the same field were satisfied, and an excellent black color was implemented.

(2) Comparative Example: Comparison with RGB Combination

C Solution: Viologen taking on the blue color and ferrocene were dissolved at a concentration of 146 mM and 146 mM, respectively in PC. 7 g of the corresponding solution and 3 g of a photocurable gel electrolyte (LiTFSi 1.4 M, curing composition 40 wt %) were mixed and appropriately stirred.

D Solution: Viologen taking on the green color and ferrocene were dissolved at a concentration of 146 mM and 146 mM, respectively in PC. 7 g of the corresponding solution and 3 g of a photocurable gel electrolyte (LiTFSi 1.4 M, curing composition 40 wt %) were mixed and appropriately stirred.

Cells were manufactured by mixing red, blue, and green (B/C/D) at various toning ratios, the transmittance was measured by the same method as described above, and the results thereof are shown in the following Table 2.

TABLE 2

|  | Y | L* | a* | B |
|---|---|---|---|---|
| RGB 1/5/4 | 1.02 | 6.97 | 13.89 | −22.07 |
| RGB 1/6/3 | 0.99 | 6.70 | 9.54 | −17.42 |
| RGB 1/7/2 | 0.96 | 6.44 | 5.20 | −12.76 |
| RGB 1/8/1 | 0.93 | 6.17 | 0.85 | −8.11 |

Through the Example and the Comparative Example, it was confirmed that the case where a*: −4±1 and b*: 1±1, which are the black specification conditions required in the same field, were satisfied could be achieved only when the first cathodic electrochromic material was essentially contained.

2. Gelation Characteristics

As a result of observing the curing uniformity of the electrochromic devices suggested in the Example and the Comparative Example, it was confirmed that no cured foreign substances such as bubbles and localized cured material aggregation that could be generated during the curing process were not generated at all, and the test device was also driven very uniformly.

Further, as a result of dismantling the device in order to confirm the state of the curing composition liquid in the test device, it was confirmed that a highly viscous gel having no flowing characteristics of the solution was prepared.

3. Repeated Driving Test

In order to confirm the difference in performance between Chemical Formula 1D and an electrochromic material of Chemical Formula 1 including an anchoring group, a cell was manufactured by joining two sheets of ITO glass with a size of 50×50 mm with the same solution composition, such that the ITO surfaces face each other so as to maintain a space gap of 90 μm. In this case, the used solution composition was violgen and ferrocene at 58 mM and 23 mM, respectively, and the remaining compositions are the same as those in the above-described Example.

Gelation characteristics, driving uniformity, and the like of the manufactured test device were excellent, regardless of whether the anchoring group was present or not.

Meanwhile, the results of repeating discoloration and decolorization 100 times by allowing each test device to be on and off at a voltage of 1.0 V for 20 seconds and 20 seconds, respectively were shown in the following Table 3.

TABLE 3

| Sample | Driving Cycle | Y(D65) | L*(D66) | a*(D65) | B*(D65) |
|---|---|---|---|---|---|
| Containing no Anchor | 0 time | 86.11 | 94.36 | −2.08 | 1.77 |
|  | 1 time | 16.82 | 48.03 | −16.19 | −11.33 |
|  | 100 times | 16.25 | 47.51 | −16.46 | −10.87 |
| Containing Anchor | 0 time | 86.95 | 94.72 | −2.68 | 3.31 |
|  | 1 time | 17.61 | 49.02 | −22.27 | −1.55 |
|  | 100 times | 81.39 | 92.30 | −5.07 | 3.98 |

As confirmed in Table 3, it was confirmed that when the anchoring group is included, deterioration in performance caused by repeated driving was severe. As a cause for the severe deterioration, it is determined that in a solution-phase electrochromic device in which the anchoring group adopts the diffusion of the electrochromic material as a main mechanism, deterioration in electrode characteristics, reduction in diffusion rate, and the like are caused by strong hydrogen bond characteristics of the anchoring group.

The invention claimed is:

1. A compound having the following Chemical Formula 1:

<Chemical Formula 1>

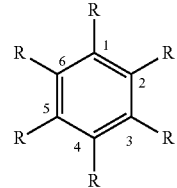

where, R is each independently selected from the group consisting of hydrogen, a halogen, a $C_1$-$C_{20}$ alkyl, a halogenated $C_1$-$C_{20}$ alkyl, an aryl group, an alkyl group linked to oxygen and nitrogen, a $C_6$-$C_{40}$ aryl group linked to oxygen and nitrogen, and a compound of the following Chemical Formula 2, with a proviso that at least three R's represent a substituent of the following Chemical Formula 2:

<Chemical Formula 2>

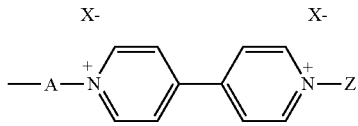

where, X−represents a counter-anion,

A is not present or is selected from the group consisting of a $C_1$-$C_{10}$ alkylene; a halogenated $C_1$-$C_{10}$ alkylene; a $C_2$-$C_{10}$ alkenylene; a halogenated $C_2$-$C_{10}$ alkenylene; a $C_2$-$C_{10}$ alkynylene; a halogenated $C_2$-$C_{10}$ alkynylene; and a heteroatom selected from N, P, O, and S, and Z is independently selected from the group consisting of a $C_1$-$C_{20}$ alkyl; a $C_1$-$C_{20}$ alkyl substituted with CN; a $C_1$-$C_{20}$ alkoxy; CN; a $C_{2-20}$ alkenyl; a $C_{2-20}$ alkynyl; a 3- to 10-membered ring cycloalkyl; a 3- to 10-membered ring heterocycloalkyl comprising a heteroatom selected from N, P, O, and S; a $C_{6-40}$ aryl; a $C_{6-40}$ aryl substituted with one or more substitution groups selected from a $C_1$-$C_{20}$ alkyl, a $C_1$-$C_{20}$ alkoxy, a $C_1$-$C_{20}$ aryloxy, a halogen, a hydroxyl, and CN; and a $C_{6-40}$ heteroaryl comprising a heteroatom selected from N, P, O, and S, with the proviso that the at least one R group that is of the Chemical Formula 2 has Z independently selected from the group consisting of a $C_1$-$C_{20}$ alkyl; a $C_1$-$C_{20}$ alkyl substituted with CN; a $C_1$-$C_{20}$ alkoxy; CN; a $C_{2-20}$ alkenyl; a $C_{2-20}$ alkynyl; a 3- to 10-membered ring cycloalkyl; and a 3- to 10-membered ring heterocycloalkyl including a heteroatom selected from N, P, O, and S, and with the proviso that the at least one R group that is of the Chemical Formula 2 has Z independently selected from the group consisting of a $C_{6-40}$ aryl; a $C_{6-40}$ aryl substituted with one or more substitution groups selected from a $C_1$-$C_{20}$ alkyl, a $C_1$-$C_{20}$ alkoxy, a $C_1$-$C_{20}$ aryloxy, a halogen, a hydroxyl, and CN; and a $C_{6-40}$ heteroaryl including a heteroatom selected from N, P, O, and S.

2. The compound of claim 1, wherein the three R's at the number 1, 3, 5 positions of Chemical Formula 1 are each independently the compound of Chemical Formula 2, and the remaining R's are independently hydrogen or a $C_1$-$C_{20}$ alkyl.

3. The compound of claim 1, wherein the A is a $C_1$—$C_{10}$ alkylene.

4. The compound of claim 1, wherein the three R's at the number 1, 3, 5 positions of Chemical Formula 1 are each independently the compound of Chemical Formula 2, and among the three R's, one R or two R's is or are selected wherein Z is independently selected from the group consisting of a $C_1$-$C_{20}$ alkyl; a $C_1$-$C_{20}$ alkyl substituted with CN; a $C_1$-$C_{20}$ alkoxy; CN; a $C_{2-20}$ alkenyl; a $C_{2-20}$ alkynyl; a 3- to 10-membered ring cycloalkyl; and a 3- to 10-membered ring heterocycloalkyl comprising a heteroatom selected from N, P, O, and S, in Chemical Formula 2, and the remaining two R's or one R are selected wherein Z is independently selected from the group consisting of a $C_{6-40}$ aryl; a $C_{6-40}$ aryl substituted with one or more substitution groups selected from a $C_1$-$C_{20}$ alkyl, a $C_1$-$C_{20}$ alkoxy, a $C_1$-$C_{20}$ aryloxy, a halogen, a hydroxyl, and CN; and a $C_{6-40}$ heteroaryl comprising a heteroatom selected from N, P, O, and S, in Chemical Formula 2.

5. The compound of claim 4, wherein the $C_{6-40}$ aryl has any one of the following structures:

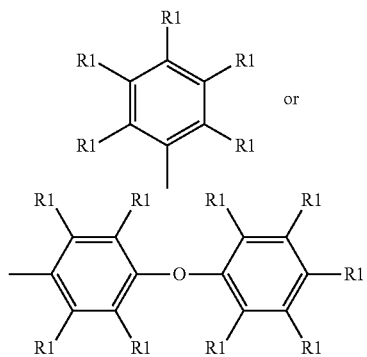

where, R1 is each independently selected from the group consisting of hydrogen, a halogen, a $C_1$-$C_{10}$ alkyl, CN, a hydroxyl, and a $C_1$-$C_{10}$ alkoxy.

6. The compound of claim 1, wherein the compound is represented by the following chemical formula:

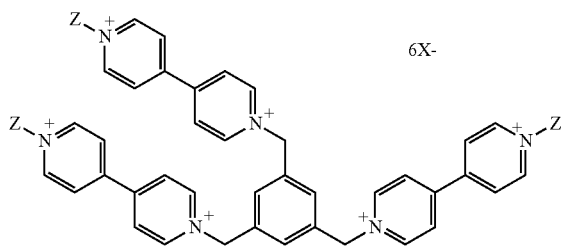

where X and Z are each independently the same as those defined in claim 1.

7. The compound of claim 1, wherein Z does not comprise an anchoring group.

8. The compound of claim 1, wherein X is selected from the group consisting of $Cl^-$, $Br^-$, $I^-$, $F^-$, $ClO_4^-$, $BF_4^-$, $PF_6^-$, and $TFSi^-$.

9. The compound of claim 1, wherein the compound exhibits electrochromic characteristics.

10. An electrochromic composition comprising the compound according to claim 1 as a cathodic electrochromic material.

11. The electrochromic composition of claim 10, wherein the electrochromic composition comprises the compound as a first cathodic electrochromic material, and further comprises a compound represented by the following chemical formula as a second cathodic electrochromic material:

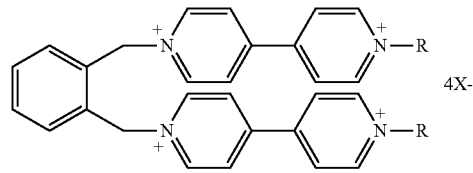

where, X- represents a counter-anion,

R is independently selected from the group consisting of a $C_1$-$C_{20}$ alkyl, a $C_1$-$C_{20}$ alkyl substituted with a $C_6$-$C_{40}$ aryl, benzyl, a 3- to 10-membered ring heterocycloalkyl comprising a heteroatom, a $C_{6-40}$ aryl, a $C_{6-40}$ aryl substituted with a $C_1$-$C_{20}$ alkyl, and a $C_{6-40}$ heteroaryl comprising a heteroatom selected from N, P, O, and S, and the second cathodic electrochromic material has discoloration characteristics in which Y is 0.93 to 1.04, L* is 8.35 to 9.35, a* is 41.03 to 46.17, and b* is −23.38 to −24.92 in the color coordinate.

12. The electrochromic composition of claim 11, wherein the second cathodic electrochromic material is represented by the following chemical formula:

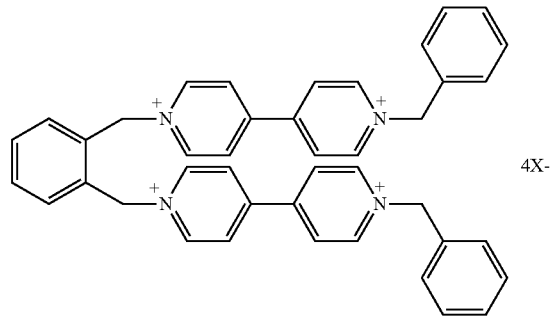

where X− represents a counter anion.

13. The electrochromic composition of claim 11, wherein a molar ratio of the first cathodic electrochromic material: the second cathodic electrochromic material is 1:1 to 500:1.

14. The electrochromic composition of claim 10, wherein the electrochromic composition further comprises a counter oxidation compound selected from the group consisting of a ferrocene-based compound and an amine-based compound.

15. The electrochromic composition of claim 14, wherein the counter oxidation compound is one or more selected from the group consisting of ferrocene, ethyl ferrocene, propyl ferrocene, t-butyl ferrocene, a $C_1$-$C_{20}$ alkyl ferrocene, a halogenated ferrocene, phenoxazine, 5,10-dihydrophenazine, N,N,N',N'-tetramethyl-p-phenylenediamine, phenothiazine, 10-methylphenothiazine, and isopropyl phenothiazine.

16. The electrochromic composition of claim 10, wherein the electrochromic composition further comprises a curing agent selected from the group consisting of an acrylic polymer, polyacrylate, polymethylmethacrylate, polyvinyl acetate, polyurethane, polystyrene, polyacetonitrile, cellulose, carboxymethyl cellulose, hydroxymethyl cellulose, cellulose propionate, hydroxypropylmethyl cellulose, gum, hydrochloride, gellan, carrageenan, pullulan, polyethylene oxide, polypropylene oxide, polyvinyl acetate, poly(N-vinyl pyrrolidone), and polyvinylindene fluoride.

17. An electrochromic device comprising:
    a compound, or an electrochromic composition comprising the compound, wherein the compound is defined according to claim 1.

18. The electrochromic device of claim 17, wherein the electrochromic device comprises a first substrate provided with a first electrode and a second substrate provided with a second electrode, and the compound or the electrochromic composition is comprised in a space between the two substrates disposed spaced apart from each other.

19. A product comprising the electrochromic device of claim 17, which is selected from the group consisting of window glass for construction, smart window, mirror for a vehicle, a display, and an electronic shelf label (ESL).

20. A method of manufacturing an electrochromic device, the method comprising:
    preparing an electrochromic solution comprising: the compound according to claim 1; a counter oxidation compound selected from a ferrocene-based compound or an amine-based compound; and a curing agent;
    preparing a cell comprising a first substrate provided with a first electrode and a second substrate provided with a second electrode, wherein the two substrates are disposed spaced apart from each other;
    injecting the prepared electrochromic solution into a space between the first substrate and the second substrate of the cell; and
    curing the injected solution.

21. The method of claim 20, wherein the electrochromic solution further comprises a compound represented by the following chemical formula as a second cathodic electrochromic material:

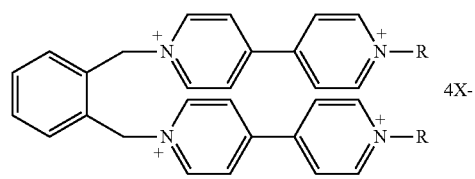

where, X– represents a counter-anion,
R is independently selected from the group consisting of a $C_1$-$C_{20}$ alkyl, a $C_1$-$C_{20}$ alkyl substituted with a $C_6$-$C_{40}$ aryl, benzyl, a 3- to 10-membered ring heterocycloalkyl comprising a heteroatom, a $C_{6-40}$ aryl, a $C_{6-40}$ aryl substituted with a $C_1$-$C_{20}$ alkyl; and a $C_{6-40}$ heteroaryl comprising a heteroatom selected from N, P, O, and S, and
the second cathodic electrochromic material has discoloration characteristics in which Y is 0.93 to 1.04, L* is 8.35 to 9.35, a* is 41.03 to 46.17, and b* is –23.38 to –24.92 in the color coordinate.

* * * * *